(12) United States Patent
Liou et al.

(10) Patent No.: US 7,946,064 B2
(45) Date of Patent: May 24, 2011

(54) DISPLAY APPARATUS WITH SCENT DISPERSE DEVICE

(75) Inventors: Guan-De Liou, Taipei (TW); Chia-Pine Huang, Keelung (TW); Li-Li Lai, Taipei (TW); Stephen Tsai, Sijhih (TW); Ming-Chun Lee, Taipei (TW)

(73) Assignee: Hannspree Inc., Taipei (TW)

( * ) Notice: Subject to any disclaimer, the term of this patent is extended or adjusted under 35 U.S.C. 154(b) by 0 days.

(21) Appl. No.: 12/765,719

(22) Filed: Apr. 22, 2010

(65) Prior Publication Data

US 2011/0049261 A1  Mar. 3, 2011

Related U.S. Application Data

(62) Division of application No. 11/843,105, filed on Aug. 22, 2007, now Pat. No. 7,757,965.

(30) Foreign Application Priority Data

Jun. 26, 2007  (TW) ............................... 96123111 A (51) Int. Cl.
| G09F 19/02 | (2006.01) |
| G09F 19/00 | (2006.01) |
| B05B 1/24 | (2006.01) |
| B05B 1/08 | (2006.01) |
| B05B 1/00 | (2006.01) |
| B05B 15/00 | (2006.01) |
| B05B 17/06 | (2006.01) |
| B05B 17/00 | (2006.01) |
| A41G 1/00 | (2006.01) |

(52) U.S. Cl. ............ 40/427; 40/429; 40/614; 239/102.2; 239/135; 239/211; 239/289; 428/17; 428/21

(58) Field of Classification Search .................... 239/34, 239/47, 53–57, 60, 102.1, 102.2, 135, 136, 239/211, 289; 40/427, 429, 459, 463–466, 40/470, 613, 614; 428/15–19, 21–24; 362/567, 362/568

See application file for complete search history.

(56) References Cited

U.S. PATENT DOCUMENTS

| 2,507,899 | A | * | 5/1950 | Gilowitz ........................ 239/44 |
| 5,077,102 | A | * | 12/1991 | Chong ............................ 428/24 |
| 5,455,750 | A | * | 10/1995 | Davis et al. ................... 362/123 |
| 6,830,733 | B2 | * | 12/2004 | Stanley, III ................... 422/124 |
| 2004/0111935 | A1 | * | 6/2004 | Tipay ............................. 40/414 |
| 2004/0197221 | A1 | * | 10/2004 | Stanley, III ....................... 422/5 |

* cited by examiner

*Primary Examiner* — Darren W Gorman
(74) *Attorney, Agent, or Firm* — Apex Juris, pllc; Tracy M Heims (57) ABSTRACT

A display apparatus with a scent disperse device includes a display, a stalk-shaped member, at least one leaf-shaped member, a vibrator and a sensor switch, in which the display is composed of a screen and at least one screen cover, the stalk-shaped member is disposed on the display to disperse scent outward, the leaf-shaped members are positioned around the stalk-shaped member and the vibrator is disposed in the stalk-shaped member and used for driving the leaf-shaped members to sway, and the sensor switch controls the opening and closing of the at least one screen cover and transmitting a starting signal. Whereby, a user is allowed to smell a flavor matching the appearance of the display or prefer scent.

6 Claims, 9 Drawing Sheets

DISPLAY APPARATUS WITH SCENT DISPERSE DEVICE

CROSS-REFERENCES TO RELATED APPLICATIONS

The present application is a divisional application of U.S. patent application Ser. No. 11/843,105, filed on Aug. 22, 2007, which is hereby incorporated by reference.

FIELD OF INVENTION

The present invention relates to a display, and more particularly to a display with scent disperse device.

BACKGROUND

A traditional cathode ray tube (CRT) display not only has a large size and a heavy weight but also generates radiant rays harmful to human; it gradually loses popularity in the display market because of so many deficits and is replaced with flat panel displays mainly liquid crystal display (LCD).

Accompanying the appreciation of esthetics economics and vogue popularity, the appearance design of the LCD is more and more diversified. However, the flat panel display in the current market still takes plastic and of alloy as main materials for shape modeling, which somewhat causes visual rigidity and stiffness. Hence, for allowing the surface quality of the display to be colorful and varied in postures, manufacturing processes such as paint coating and transfer printing are mostly adopted to process surface treatment and secondary processing to enable the appearance of LCD to attain to the visional emulation effect.

Although the appearance of LCD has already been provided with the visional emulation effect, it still cannot provide proper and emulative quality of scent matching the appearance of the display. Hence, for display structure to allow it to not only be provided a visional emulation effect, but also offer a emulative quality of scent matching the display and further to built a mood more suitable for program viewing, the present invention is proposed.

SUMMARY

For improving the deficits mentioned above, the present invention discloses a display apparatus with scent disperse device.

The present invention provides a display apparatus with a scent disperse device comprising a display, a stalk-shaped member, at least one leaf-shaped member, a vibrator and a sensor switch. The display is composed of a screen and at least one screen cover used for covering the screen. The stalk-shaped member is disposed on the display and is composed of a housing, at least one dispersing spray hole positioned on a surface of the housing, and a fragrant material dispersing scent outward through the at least one dispersing spray hole. The leaf-shaped members are positioned around the stalk-shaped member; the vibrator is disposed in the stalk-shaped member, butted against or connected to the leaf-shaped members and used for driving the leaf-shaped members to sway; the sensor switch controls the opening and closing of the at least one screen cover and transmitting a starting signal.

The stalk-shaped member and the leaf-shaped members disposed on the display according to the present invention not only allows the display to be provided with emulative outlook vision but also enable a user to smell a flavor matching the appearance of the display and his favorite scent so as to attain to the olfaction emulating object.

Besides, the leaf-shaped members are allowed to sway through the vibrator according to the present invention to enable the undulation amplitude of the leaf-shaped member not only to simulate a true leaf swaying state but also help dispersing scent to attain to the fast scent diffusing effect.

BRIEF DESCRIPTION OF THE DRAWINGS

The present invention can be more fully understood by reference to the following description and accompanying drawings, in which.

DETAILED DESCRIPTION

Figure 1:
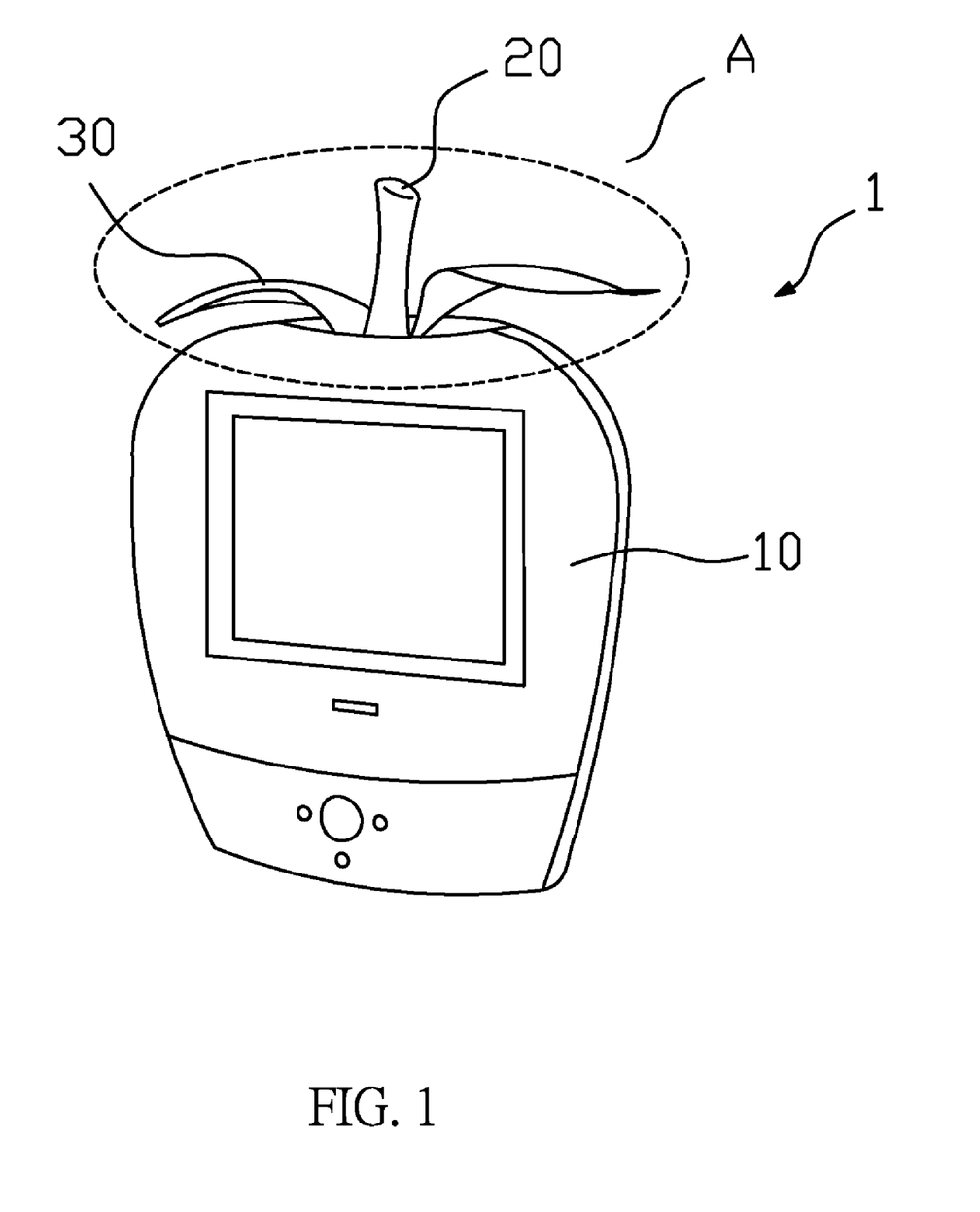
FIG. 1 is a schematically perspective view, showing a display apparatus with scent disperse device of a first preferred embodiment according to the present invention.
Figure 2A:
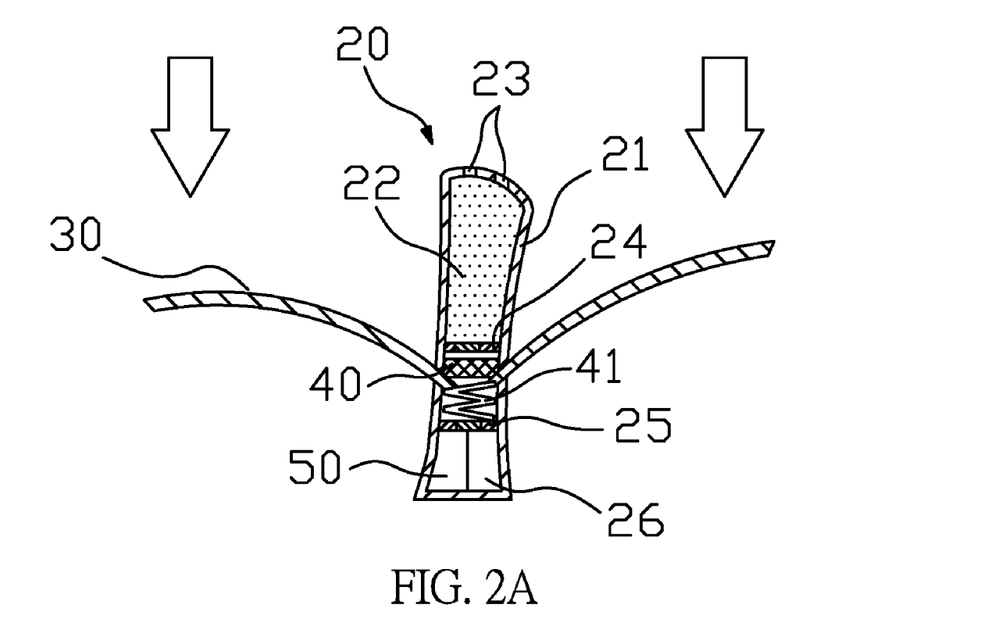
FIG. 2A is a cross sectional view, showing a part A of FIG. 1 in which leaf-shaped members are in a static state.
Figure 2B:
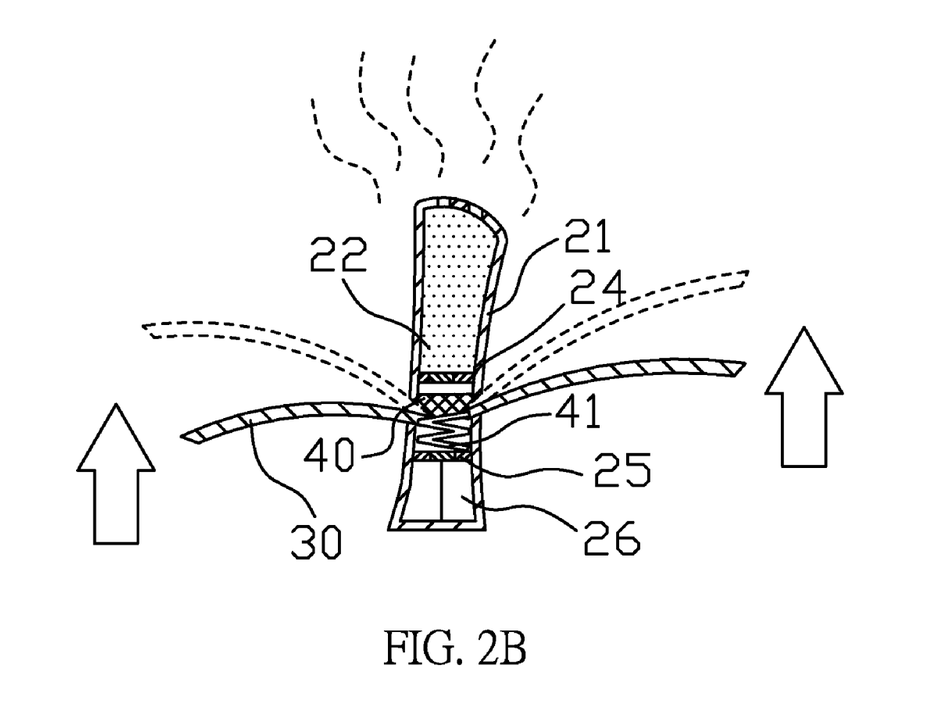
FIG. 2B is a cross sectional view, showing a part A of FIG. 1 in which leaf-shaped members are caused to sway.

Please refer to FIGS. 1, 2A and 2B. FIG. 1 is a schematically perspective view, showing a display apparatus with scent disperse device of a first preferred embodiment according to the present invention. FIG. 2A is a cross sectional view, showing a part A of FIG. 1 in which leaf-shaped members are in a static state. FIG. 2B is a cross sectional view, showing a part A of FIG. 1 in which leaf-shaped members are caused to sway.

A scent disperse display apparatus 1 includes a display 10, a stalk-shaped member 20, a plurality of leaf-shaped members 30 and a vibrator 40.

A periphery of the display 10 is provided with a body with shape similar to a fruit and a stalk-shaped member 20 is disposed on the display 10, in which sides of the stalk-shaped member 20 are disposed with leaf-shaped members 30 to allow the entire appearance looking like a fruit (e.g. apple, orange) and have an emulative outlook vision thereof. Besides, a vibrator 40 butted against or connected to the leaf-shaped members 30 is disposed in the stalk-shaped member 20 and used for driving the leaf-shaped members 30 to sway, in which the undulation amplitude of the leaf-shaped member 30 simulate a true leaf swaying state. Furthermore, an elastic element 41 butted against or connected to the leaves is disposed below the vibrator 40 and used for supporting the vibrator 40. Here, the elastic element 41 can be a spring or an element capable of elastically supporting the vibrator 40.

The stalk-shaped member 20 mentioned above includes a housing 21, a fragrant material 22 and a plurality of disperse holes 23, in which the fragrant material 22 is stored in the housing 21 and used for generating scent and the plurality of disperse holes 23 are disposed on the surface of the housing 21 and allows the fragrant material 22 to disperse the scent outward through the disperse holes 23. Please refer to FIGS. 2A, 2B and 9 simultaneously. A piezoelectric sheet 24, a circuit board 25 and a power supply 26 can be further installed in the housing 21 according to the present invention, in which the circuit board 25 is respectively electrically connected to the vibrator 40, the piezoelectric sheet 24 and the power supply 26. The power supply 26 is used for providing power source for the circuit board 25; logic operation and signal transceiver circuits (not shown in the figure) are disposed on the circuit board 25 and used for receiving, operating and transmitting signals with specific functions or specific receiving terminal (e.g. the piezoelectric sheet 24 and the vibrator 40 in the present embodiment); the piezoelectric sheet 24 is conducted to generate heat energy to cause the fragrant material 22 to disperse scent outward after receiving a conducting signal S2 transmitted from the circuit board 25.

In addition, the display apparatus 1 according to the present invention further includes a sensor switch 50 electrically connected to the circuit board 25 and can be disposed on the display 10 or in the stalk-shaped member 20 as FIG. 2A shows. The sensor switch 50 will transmit a starting signal S1 to the circuit board 25 after being activated. Thereafter, the circuit board 25 alone further transmit the aforementioned conducting signal S2 to the piezoelectric sheet 24 to cause it to be conducted to generate heat energy after the circuit board 25 receives and operates the starting signal S1 or further transmit a vibrating signal S3 to the vibrator 40 at the same time to start the vibrator 40 to drive the leaf-shaped members 30 to sway simultaneously. Here, the sensor switch 50 processes sensing through infrared ray (infrared ray sensor switch) or light shielding effect (light shielding sensor switch).

Therefore, when a user moves near to the display 10, the sensor switch 50 will sense the approach of the user and activate the heating of the piezoelectric sheet 24 and the vibrator 40 as mentioned above to cause the fragrant material 23 to disperse scent outward via the disperse holes 23 and drive the leaf-shaped members 30 to sway up and down through the vibrator 40 to boost the scent to disperse quickly so as to enable the user to smell the scent matching the appearance of the display 10 (e.g. smell of an apple or orange) and in the meantime, the vision and the smell emulations can be attained simultaneously.

Figure 3:
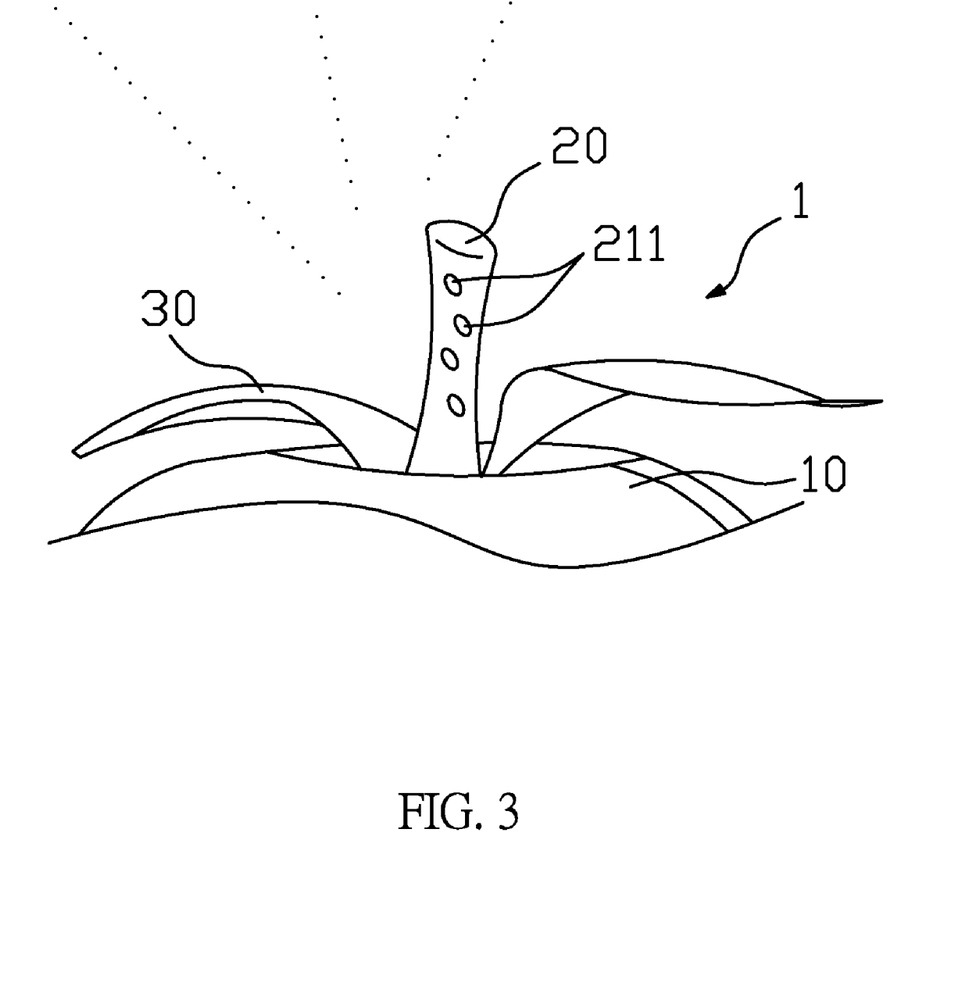
FIG. 3 is a schematic view, showing a stalk-shaped member of a display apparatus with a scent disperse device of a second preferred embodiment according to the present invention.

Please refer to FIG. 3. FIG. 3 is a schematic view, showing a stalk-shaped member 20 of a display apparatus with a scent disperse device of a second preferred embodiment according to the present invention.

The stalk-shaped member 20 of the present invention can be manufactured by mixing the rubber or plastic material with fragrance; scent is generated through the fragrance and quickly disperse through the boosting of the vertical swaying of the leaf-shaped member 30 so as to allow the user to smell the scent when he moves near to the display 10.

Besides, a plurality of fragrance micelles 211, which can sense friction, temperature or electric field to generate scent, can be disposed on a surface of the housing 21, in which a diameter of the fragrance micelle 211 is 5 to 5000 micrometers, but the fragrance micelle 211 with diameter over 20 micrometers can rather exhibit the effect of the present invention. Whereby, the stalk-shaped member 20 is allowed to disperse the scent for a long period of time and the user can also use hand temperature, friction and etc to bring the fragrance micelles 211 to generate scent by touching the stalk-shaped member 20 to attain to the scent disperse controlling object.

When the sensor switch 50 senses the approach of the user, it will transmit a starting signal S1 to the circuit board 25 as described in the first embodiment, the circuit board 25 then transmit a vibrating signal S3 to cause the vibrator 40 to vibrate after the operation thereof and the vibrator 40 drives the leaf-shaped members 30 to sway to assist the scent to be disperse to enable it to spread quickly to allow the user to smell the scent matching the appearance of the display 10 and in the meantime, the vision and the olfaction emulation objects and be attained.

Figure 4:
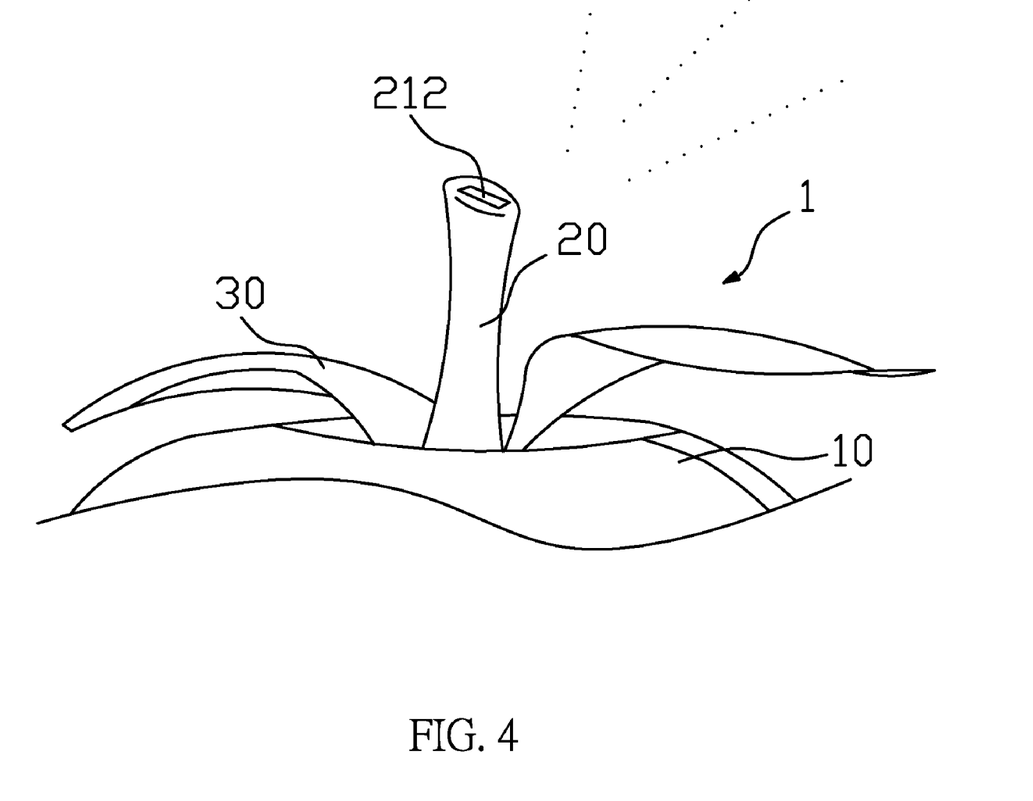
FIG. 4 is a schematic view, showing a stalk-shaped member of a display apparatus with a scent disperse device of a third preferred embodiment according to the present invention.

Please refer to FIG. 4. FIG. 4 is a schematic view, showing a stalk-shaped member 20 of a display apparatus with a scent disperse device of a third preferred embodiment according to the present invention.

According to the structure disclosed by the present invention, a fragrance insert 212 used for generating scent can also be installed on the housing 21. When the vibrator 40 drives the leaf-shaped members 30 to sway up and down, it can help the scent of the fragrance insert 212 to disperse quickly. Besides, a new fragrance insert 212 can also be replaced to maintain the scent from the stalk-shaped member 20 when the scent fragrance insert 212 on the housing 21 fades.

Figure 5:
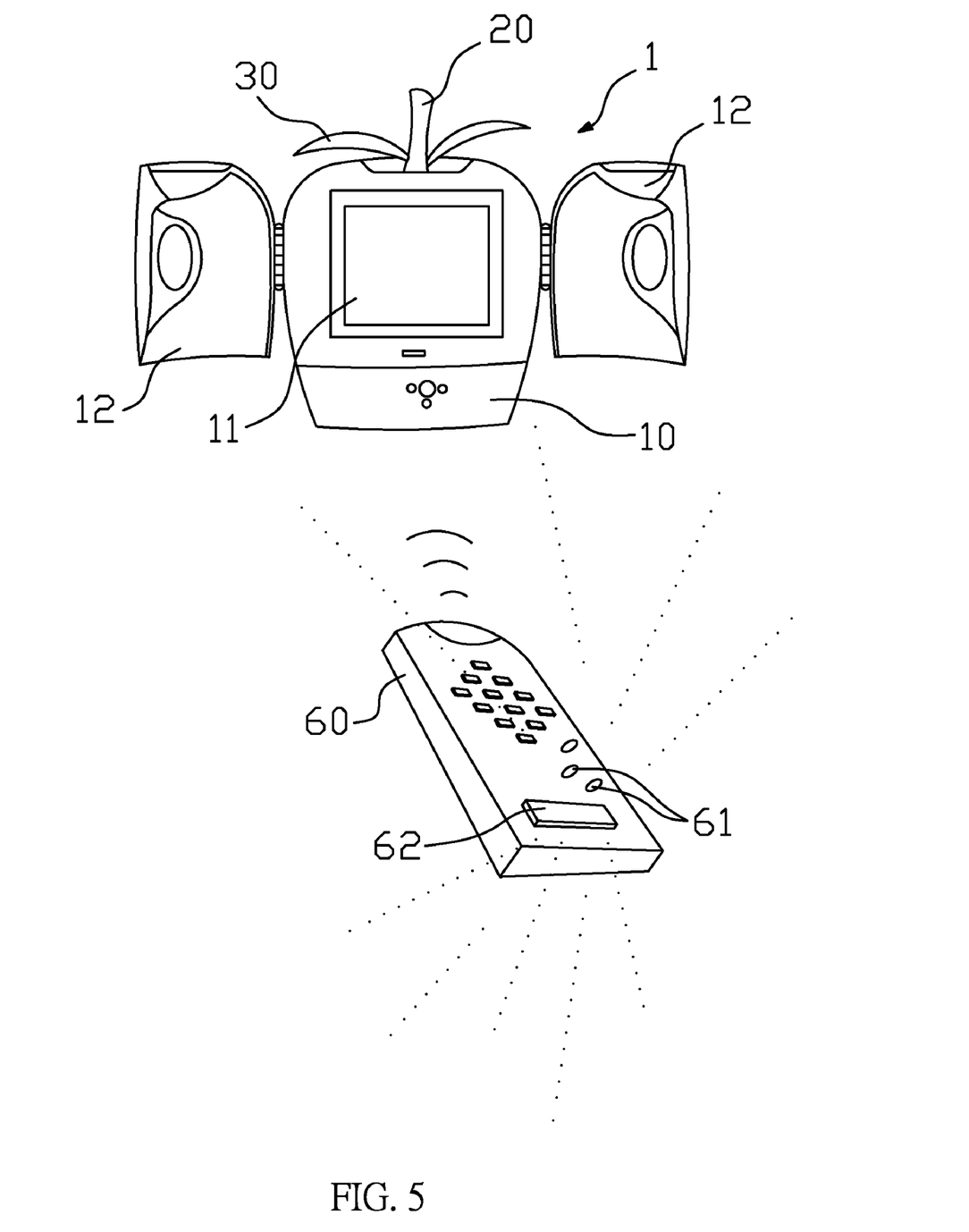
FIG. 5 is a schematically perspective view, showing a display apparatus with a scent disperse device of a fourth preferred embodiment according to the present invention.
Figure 6A:
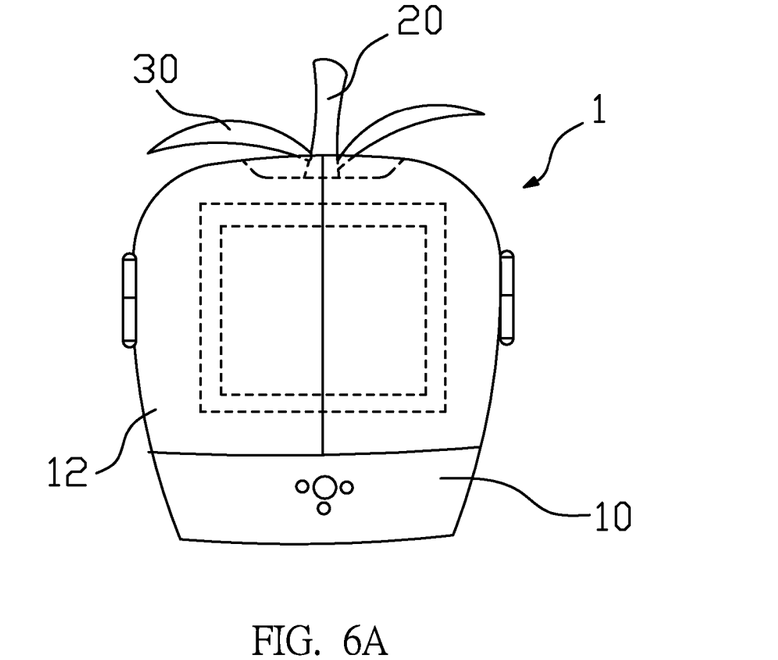
FIG. 6A is a schematic view, showing the display apparatus with a scent disperse device of the fourth preferred embodiment according to the present invention in which screen covers are closed.
Figure 6B:
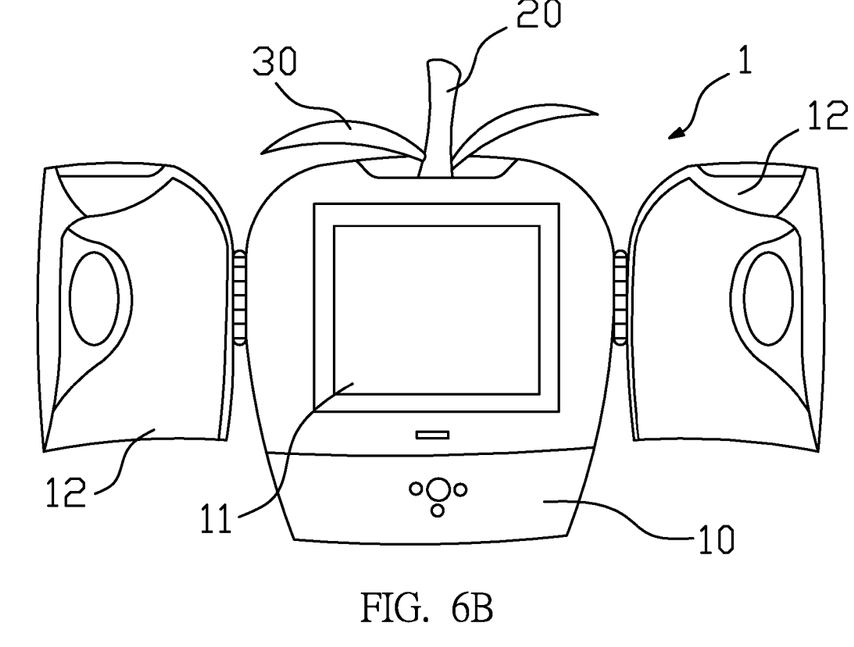
FIG. 6B is a schematic view, showing the display apparatus with a scent disperse device of the fourth preferred embodiment according to the present invention in which screen covers are opened.
Figure 9:
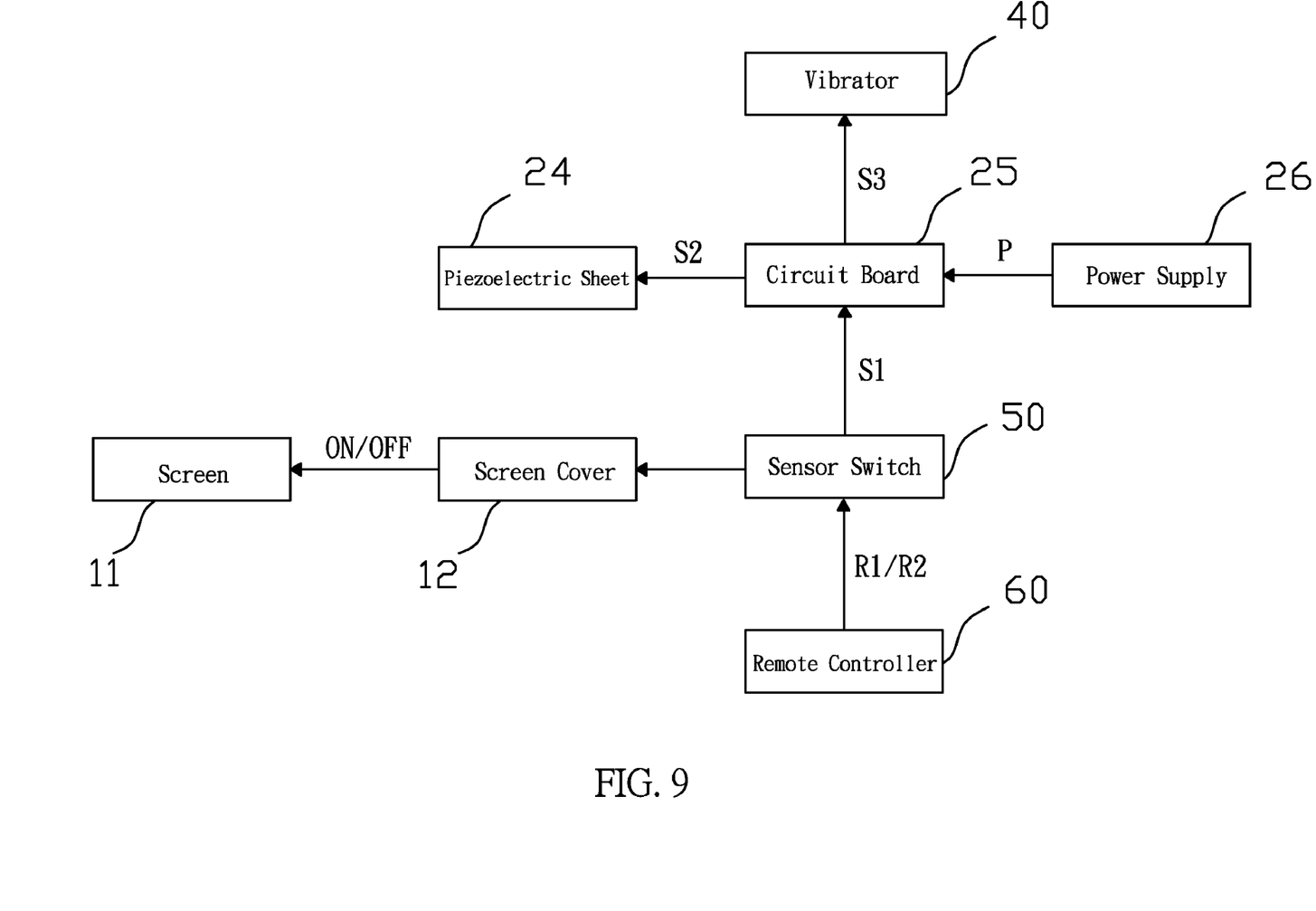
FIG. 9 is a block diagram, showing an electric connection of components of the display apparatus with a scent disperse device of the first preferred embodiment according to the present invention.

Please refer to FIGS. 5, 6A, 6B and 9. FIG. 5 is a schematically perspective view, showing a display apparatus with a scent disperse device of a fourth preferred embodiment according to the present invention. FIG. 6A is a schematic view, showing the display apparatus with a scent disperse device of the fourth preferred embodiment according to the present invention in which screen covers are closed. FIG. 6B is a schematic view, showing the display apparatus with a scent disperse device of the fourth preferred embodiment according to the present invention in which screen covers are opened. FIG. 9 is a block diagram, showing an electric connection of components of the display with a scent disperse device of the first preferred embodiment according to the present invention.

The display apparatus 1 with a scent disperse device according to the present invention further includes a remote controller 60, and the display 10 includes a screen 11 and a plurality of screen cover 12, in which the screen cover 12 are electrically connected to the sensor switch 50 so as to allow them to be opened or closed through the sensor switch, the user can transmit a first starting signal R1 through the remote controller 60 to start the display 10 and chose a program that he wants to view. Besides, the remote controller 60 can use the aforementioned first starting signal R1 or further transmits a second starting signal R2 to start the sensor switch 50, the sensor switch 50 then starts the piezoelectric sheet 24 and the vibrator 40 electrically connected therewith through the circuit board 25 as described in the first embodiment to cause the fragrant material 22 to disperse scent outward through the disperse holes 23 and drive the leaf-shaped members 30 to sway up and down to help the scent to be dispersed quickly through the vibrator 40. Moreover, because the screen cover 12 is electrically connected to the screen 11, when the screen cover are opened, a starting signal ON is transmitted to start the power supply of the screen 11 and vice versa, when the screen cover are closed, a close signal OFF is sent out to close the power source of the screen 11.

A surface constituting material of the remote controller 60 can be manufactured by mixing the rubber or plastic material with fragrance so as to generate scent through the fragrance. Besides, a surface of the remote controller can also disposed with a plurality of fragrance micelles 61; a dimension of the fragrance micelle 61 is the same as the fragrance micelle 211 mentioned above, and the fragrance micelle 61 can sense friction, temperature or electric field to generate scent. When the user operates the remote controller 60, he can use hand temperature to bring the fragrance micelles 91 to generate scent so as to control the disperse of the scent of the fragrance micelles 61.

Furthermore, a fragrance insert 62 can also be further installed on the remote controller 60 so as to generate scent through the fragrance insert 62 and maintain the scent disperse by the remote controller 60 by replacing it with a new fragrance insert 62.

Figure 7:
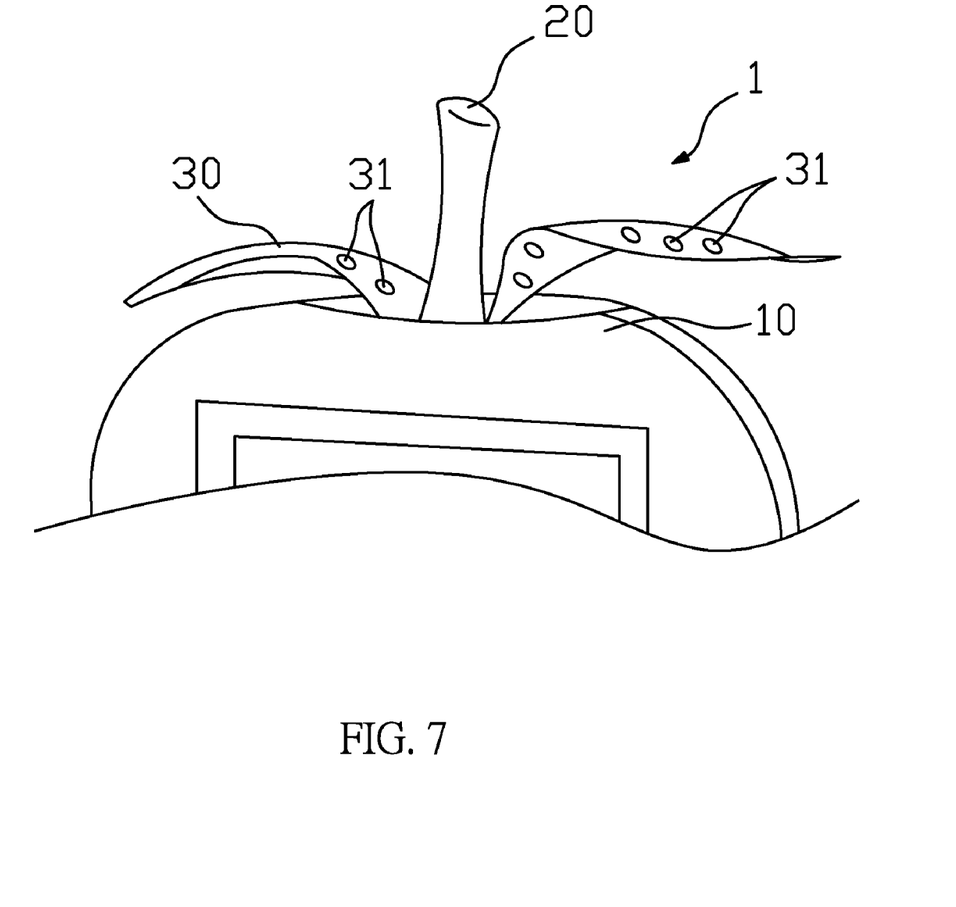
FIG. 7 is a schematic view, showing leaf-shaped members of a display apparatus with a scent disperse device of a fifth preferred embodiment according to the present invention.

Please refer to FIG. 7. FIG. 7 is a schematic view, showing leaf-shaped members 30 of a display apparatus with a scent disperse device of a fifth preferred embodiment according to the present invention.

The leaf-shaped members 30 of the present invention can be manufactured by mixing rubber or plastic material with fragrance, and the leaf-shaped members 30 are driven to sway to help the scent to be dispersed quickly through the vibrator 40 so as to allow the user to smell scent when he moves near to the display 10.

According to the structure disclosed by the present invention, a plurality of fragrance micelles 31 can also be installed in the leaf-shaped members 30, in which a dimension of the fragrance micelle is the same as the fragrance micelle 211 mentioned above, and the fragrance micelle 21 can sense friction, temperature or electric field to generate scent so as to allow the stalk-shaped member 20 to disperse scent in a long time, to allow the user to use hand temperature, friction and etc to bring the fragrance micelles 31 to generate scent by touching the leaf-shaped members 30 so as to control the disperse of the scent of the fragrance micelles 61.

When the scent disperses by the leaf-shaped members 30 fades, they can be replaced with new leaf-shaped members 30 to maintain the scent.

Figure 8:
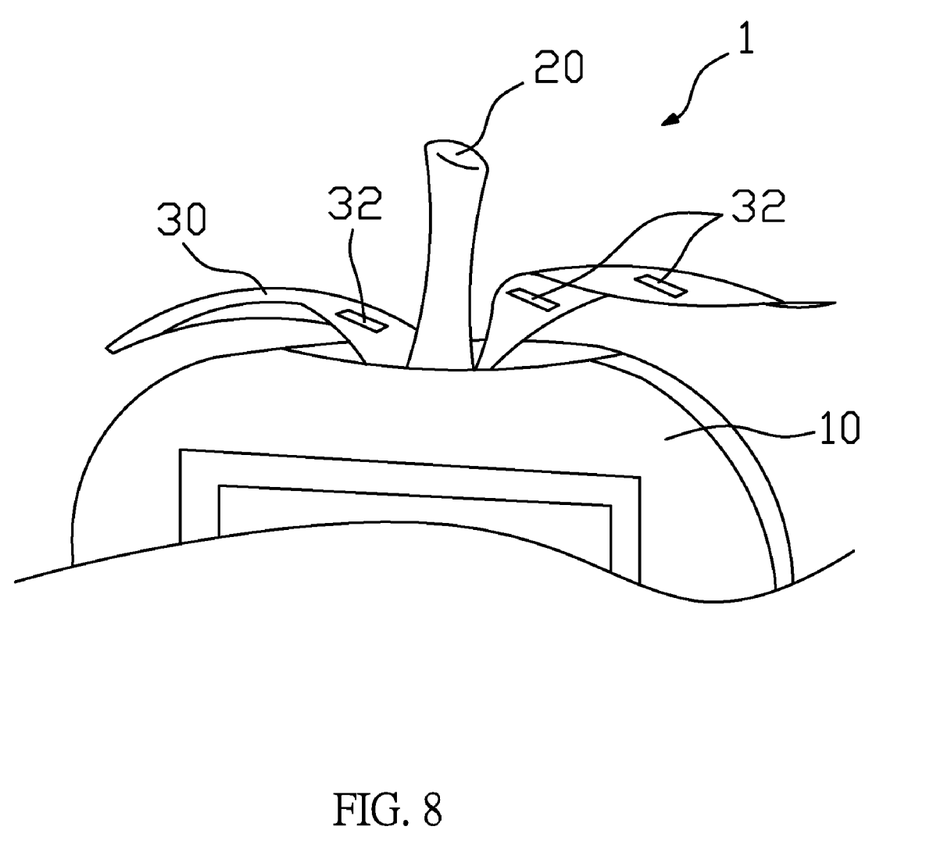
FIG. 8 is a schematic view, showing leaf-shaped members of a display apparatus with a scent disperse device of a sixth preferred embodiment according to the present invention.

Please refer to FIG. 8. FIG. 8 is a schematic view, showing leaf-shaped members 30 of a display apparatus with a scent disperse device of a sixth preferred embodiment according to the present invention.

Besides, a plurality of fragrance insert 32 used for generating scent can also be installed on the leaf-shaped members 30. When the vibrator 40 drives the leaf-shaped members 30 to sway up and down, it can help the scent of the fragrance insert 32 to be dispersed quickly. Furthermore, when the scent of the fragrance insert 32 on the leaves 30 fades, they can be replaced with new fragrance insert 32 to maintain the scent.

The entire appearance of the display 10, the stalk-shaped member 20 and the leaf-shaped members 30 is allowed to look like a fruit (e.g. apple, orange) through the structure disclosed by the present invention; it is provided with a emulative outlook vision and allows the stalk-shaped member 20 and the leaf-shaped members 30 to disperse scent in the meantime, the vertical swaying of the leaf-shaped members 30 helps the scent disperse, allows the user to smell the scent (e.g. apple scent, orange scent) matching the appearance of the display 10. Whereby, the vision and the olfaction emulation objects can be attained simultaneously and the mood more suitable for viewing a program can be further built. Besides, the user can use hand temperature, friction and etc to bring the stalk-shaped member 20 and the leaf-shaped members 30 to generate scent so as to enable the user to control the disperse of the scent. Furthermore, when the scent fades, the weakening scent component can be replaced with a new one to maintain the scent disperse by the display apparatus of the present invention.

The component inbuilt with the plurality of scent micelles 211, 31 or 61 mentioned above can be manufactured by means of pouring or injection after the fragrance micelles 211, 34 or 61 are added into rubber or plastic material particles and uniformly stirred. The technology of placing the fragrance micelles 211, 31 or 61 into the rubber or plastic is adopted in the present invention to improve a peculiar and unbearable smell of a convention rubber or plastic material and increase the term of validity of dispersing a scent.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A display apparatus with a scent disperse device, comprising:
   a display, comprising;
      a screen; and
      at least one screen cover, used for covering the screen;
   a stalk-shaped member, disposed on the display; wherein the stalk-shaped member comprises
      a housing;
      a fragrant material, stored in the housing; and
      at least one dispersing spray hole, positioned on a surface of the housing, the fragrant material dispersing scent outward through the at least one dispersing spray hole;
   at least one leaf-shaped member, disposed around the stalk-shaped member;
   a vibrator, disposed in the stalk-shaped member, butted against or connected to the leaf-shaped members and used for driving the leaf-shaped members to sway wherein said vibrator comprises an elastic element, disposed below the vibrator, butted against or connected to the leaf-shaped members, and used for supporting the vibrator;
   a piezoelectric sheet, disposed in close proximity to the fragrant material in the housing, used for electrical conduction to generate heat energy to cause the fragrant material to disperse scent outward;
   a circuit board and a power supply, disposed in the stalk shaped member, the circuit board being electrically connected to the vibrator, the piezoelectric sheet and the power supply, the power supply being used for providing a power source for the circuit, and the circuit board being used for receiving, operating or transmitting a signal with a specific function; and
   a sensor switch, electrically connected to the at least one screen cover and the circuit board, used for controlling the opening and closing of the at least one screen cover and transmitting a starting signal to the circuit board after being activated, a conducting signal being then transmitted to the piezoelectric sheet to allow electrical conduction of the piezoelectric sheet to generate heat energy after the circuit board receives and operates the starting signal.

2. The display apparatus according to claim 1, wherein the at least one screen cover is electrically connected to the screen, a starting signal is transmitted to start a power supply of the screen when the at least one screen cover is opened and a close signal is transmitted to close the source of the screen when the at least one screen cover is closed.

3. The display apparatus according to claim 1, further comprising a remote controller used for starting the display or the sensor switch.

4. The display apparatus according to claim 3, further comprising a plurality of fragrance micelles disposed on a surface of the remote controller to disperse scent.

5. The display apparatus according to claim 3, wherein a surface of the remote controller is manufactured by mixing rubber or plastic material with fragrance.

6. The display apparatus according to claim 3, further comprising a fragrance insert disposed on the remote controller to disperse scent.

* * * * *